US012797400B2

(12) United States Patent
Turski

(10) Patent No.: US 12,797,400 B2
(45) Date of Patent: Nov. 17, 2026

(54) NEUTRAL ENDOPEPTIDASE (NEP) AND HUMAN SOLUBLE ENDOPEPTIDASE (hSEP) INHIBITORS FOR PROPHYLAXIS AND TREATMENT OF EYE DISEASES

(71) Applicant: Christopher Turski, Waunakee, WI (US)

(72) Inventor: Christopher Turski, Waunakee, WI (US)

(73) Assignee: Christopher Turski, Waunakee, WI (US)

(*) Notice: Subject to any disclaimer, the term of this patent is extended or adjusted under 35 U.S.C. 154(b) by 0 days.

(21) Appl. No.: 17/978,442

(22) Filed: Nov. 1, 2022

(65) Prior Publication Data

US 2023/0118503 A1 Apr. 20, 2023

Related U.S. Application Data

(62) Division of application No. 16/963,234, filed as application No. PCT/PL2019/000012 on Jan. 31, 2019, now abandoned.

(30) Foreign Application Priority Data

Jan. 31, 2018 (PL) ...................................... P.424452

(51) Int. Cl.
*A61K 31/685* (2006.01)
*A61K 31/55* (2006.01)
*A61P 27/02* (2006.01)

(52) U.S. Cl.
CPC ............ *A61K 31/685* (2013.01); *A61K 31/55* (2013.01); *A61P 27/02* (2018.01)

(58) Field of Classification Search
None
See application file for complete search history.

(56) References Cited

U.S. PATENT DOCUMENTS

| | | | | |
|---|---|---|---|---|
| 5,677,297 | A * | 10/1997 | Waldeck | C07K 5/06139 514/211.06 |
| 5,952,327 | A | 9/1999 | Waldeck | |
| 6,998,398 | B2 | 2/2006 | van der Eerden et al. | |
| 2003/0176356 | A1 * | 9/2003 | Yorio | A61K 9/0019 514/16.1 |
| 2005/0153936 | A1 | 7/2005 | Ikonomidou | |

OTHER PUBLICATIONS

Gupta, Neeruabcd; Yücel, Yeni Habce. Glaucoma as a neurodegenerative disease. Current Opinion in Ophthalmology 18(2):p. 110-114, Mar. 2007. (Year: 2007).*

CDC. Prevention. Retrieved from the Internet on Jan. 3, 2024, https://www.cdc.gov/pictureofamerica/pdfs/picture_of_america_prevention.pdf. (Year: 2024).*

McGrady, N. R., Minton, A.Z., Stankowska, D.L. et al. Upregulation of the endothelin A (ETA) receptor and its association with neurodegeneration in a rodent model of glaucoma. BMC Neurosci 18, 27 (2017). (Year: 2017).*

Xi et al. Apoptosis in glaucoma: A new direction for the treatment of glaucoma (Review), Molecular Medicine Reports 29: 82, published 2024. (Year: 2024).*

NIH National Eye Institute. Glaucoma. Retrieved from the Internet on Apr. 10, 2025, https://www.nei.nih.gov/learn-about-eye-health/eye-conditions-and-diseases/glaucoma (Year: 2025).*

NIH National Human Genome Research Institute. About Retinitis Pigmentosa. Retrieved from the Internet on Apr. 1, 2026, https://www.genome.gov/Genetic-Disorders/Retinitis-Pigmentosa. Published 2013. (Year: 2013).*

Diaz-Coranguez M, Ramos C, Antonetti DA (2017) The inner blood-retinal barrier: Cellular basis and development. Vision Res 139, 123-137. doi:10.1016/j.visres.2017.05.009.

Good TJ, Kahook MY (2010) The role of endothelin in the pathophysiology of glaucoma. Exp Opinion Ther Targets 14, 647-654. doi:10.1517/14728222.2010.487065.

Mead B, Tomarev S (2016) Evaluating retinal ganglion cell loss and dysfunction. Exp Eye Res 151, 96-106. doi:10.1016/j.exer.2016.08.006.

Prasanna G, Krishnamoorthy R, Yorio T (2011) Endothelin, astrocytes and glaucoma. Exp Eye Res 93, 170-177. doi:10.1016/j.exer.2010.09.006.

Rosenthal R, Fromm M (2011) Endothelin antagonism as an active principle for glaucoma therapy. Br J Pharmacol 162, 806-816. doi:10.1111/j.1476-5381.2010.01103.x.

Smith CA, Vianna JR, Chauhan BC (2017) Assessing retinal ganglion cell damage. Eye 31, 209-217. doi:10.1038/eye.2016.295.

Torriglia A, Jaadane I, Lebon C (2016) Mechanisms of cell death in neurodegenerative and retinal diseases: common pathway? Curr Opinion Neurol 29, 55-60.

Wolfensberger TJ et al. (1994) Evidence for a new role of natriuretic peptides: control of intraocular pressure. Brit J Ophthalmol 78, 446-448. doi:10.1136/bjo.78.6.446.

(Continued)

*Primary Examiner* — Lauren Wells
(74) *Attorney, Agent, or Firm* — Honigman LLP; Joseph A. Mahoney; Jonathan P. O'Brien

(57) ABSTRACT

The invention pertains to a method of prophylaxis and/or treatment of an optic or eye disease in a person in need thereof, wherein the optic or eye disease is selected from the group of diseases consisting of: (i) all forms of primary and secondary glaucoma; (ii) acquired macular disorders; (iii) optic neuropathy; (iv) optic neuritis; (v) uveitis; (vi) hereditary fundus dystrophies; (vii) retinal vascular diseases; (viii) scleritis and episcleritis; (ix) retinal detachments; (x) trauma to the eye globe; (xi) vitreous opacities; (xii) myopia and degenerative myopia; (xiii) postsurgical trauma; (xiv) dry eye disease; (xv) corneal disorders; and wherein the method comprises administering to said person a benzazepine, benzoxazepine, benzothiazepine-N-acetic acid and phosphono-substituted benzazepinone derivatives having both neutral endopeptidase (NEP) and/or human soluble endopeptidase (hSEP), and endothelin convertase (ECE) inhibitory activity.

27 Claims, No Drawings

(56) References Cited

OTHER PUBLICATIONS

A Phase 2a Dose Escalation Study with SLV334 in Patients with Traumatic Brain Injury, ClinicalTrials.gov, NCT00735085 (last update posted Sep. 21, 2011).
Ishimaru, M.J. et al., Distinguishing Excitotoxic from Apoptotic Neurodegeneration in the Developing Rat Brain, J. Comp. Neuro. 408: 461-476 (1999).
Cordeiro, M.F., et al. Imaging Apoptosis in the Eye, Eye, v.25, pp. 545-553, 2011.
Dickstein, K., et al. Effects of Single Dose of SLV306, an Inhibitor of Both Neutral Endopeptidase and Endothelin-Converting Enzyme, on Pulmonary Pressures in Congestive Heart Failure, American Journal of Cardiology, v.94, pp. 237-239, 2004.
Fernandez-Albarral, J.A., et al. Glaucoma: From Pathogenic Mechanisms to Retinal Glial Cell Response to Damage, Frontiers in Cellular Neuroscience, v.18, Jan. 24, 2024.
National Eye Institute, Glaucoma Surgery, https://www.nei.nih.gov/learn-about-eye-health/eye-conditions-and-diseases/glaucoma, retrieved Oct. 5, 2025.
Parvanova, A., et al. Effect on Blood Pressure of Combined Inhibition of Endothelin-Converting Enzyme and Neutral Endopeptidase with Daglutril in Patients with Type 2 Diabetes Who Have Albuminuria: A Randomize, Crossover, Double-Blind, Placeo-Controlled Trial, The Lancet Diabetes & Endocrinology, v.1(1), pp. 19-27, 2013.
Perfuse Therapeutics, Perfuse Therapeutics Announces Positive Results from Phase 2 Clinical Trials in Glaucoma and Diabetic Retinopathy Patients, Jun. 24, 2025.
Sarkis, S., et al. Challenging Glaucoma with Emerging Therapies: An Overview of Advancements Against the Silent Thief of Sight, Frontiers in Medicine, v.12, Mar. 25, 2025.

* cited by examiner

NEUTRAL ENDOPEPTIDASE (NEP) AND HUMAN SOLUBLE ENDOPEPTIDASE (hSEP) INHIBITORS FOR PROPHYLAXIS AND TREATMENT OF EYE DISEASES

FIELD OF THE INVENTION

Described are dual inhibitors of endothelin converting enzyme-1 (ECE-1), and neutral endopeptidase (NEP) and/or human soluble endopeptidase (hSEP) alone, and compositions thereof, with the proviso that said pharmaceutical compositions may optionally contain either one or more of carbonic anhydrase inhibitors such as e.g. brinzolamide, $\alpha_2$-adrenergic agonists such as e.g. brimonidine, β-blockers such as e.g. timolol, prostaglandin analogs such as e.g. bimatoprost, rho kinase inhibitors such as e.g. netarsudil, adenosine $A_1$ receptor agonists such as e.g. trabodenoson, $ET_A$ endothelin receptor antagonists such as e.g. sitaxentan, dual endothelin receptor antagonists such as e.g. bosentan, nitric oxide donors such as e.g. butanediol, parasympathomimetics such as e.g. pilocarpine, acetylcholine, catecholamines such as e.g. adrenaline, muscarinic receptor antagonists such as e.g. atropine, vascular endothelial growth factor inhibitors such as e.g. ranibizumab, corticosteroids such as e.g. dexamethasone, antibiotics such as e.g. vancomycin, tissue regenerating agents such as e.g. polycarboxymethylglucose, vitamins and provitamins such as e.g. panthenol and retinyl palmitate, chemotherapeutic agents such as e.g. mitomycin, nonsteroidal anti-inflammatory drugs such as e.g. ketorolac, $H_1$ receptor antagonists such as e.g. cetirizine, monoclonal antibodies such as e.g. adalimumab, proteases such as e.g. ocriplasmin, immunosuppressive agents such as e.g. cyclosporine, or none, for prophylaxis and/or treatment of eye diseases.

SCIENTIFIC BACKGROUND OF THE INVENTION

An increased intraocular pressure and reduced ocular blood flow are the major risk factors for glaucoma in humans. Glaucoma is the most common optic nerve head neuropathy and is associated morphologically with loss of retinal ganglion cells and clinically with visual field deterioration. Treatment of glaucoma is based on lowering of intraocular pressure and preventing the occurrence or progression of optic neuropathy. No therapy is currently available to mitigate ocular blood flow changes during glaucoma, or to limit the death of retinal ganglion cells by means of apoptosis in the course of glaucoma (B. C. Chauhan (2008) Can. J. Ophthalmol. 43, 356-360).

Endothelin is the human body's most potent vasoactive peptide known to date. As connoted by the term vasoactive peptide, this peptide participates in the regulation of intraocular blood pressure by means of vasoconstrictor activity. Upon release it causes a decrease in ocular blood flow followed by pathology in the retina and the optic nerve head.

Endothelin, apart from its vasoconstrictor activity, participates in the regulation of intraocular pressure by means of affecting trabecular outflow, which is the main route for fluid outflow from the eye. Endothelin increases contractility of the trabecular meshwork and therefore decreases fluid outflow from the eye elevating intraocular pressure followed by pathology in the retina and the optic nerve head.

Endothelin, apart from affecting intraocular blood pressure and regulating intraocular fluid pressure, influences apoptosis of retinal ganglion cells acting via $ET_B$ receptors and induces proliferation of human optic nerve head astrocytes acting via both $ET_A$ and $ET_B$ receptors (G. Prasanna, R. Krishnamoorthy, A. F. Clark, R. J. Wordinger & T. Yorio (2002) Invest. Ophthalmol. Vis. Sci. 43, 2704-2713).

Endothelin is a peptide composed of 21 amino acids that is synthesized and released by the endothelium. Endothelin is produced by cleavage of a Trp-Val bond in the precursor peptide big endothelin (Big ET-1). Endothelin converting enzyme-1 (ECE-1), a membrane-bound metalloprotease, catalyses proteolytic activation of Big endothelin-1 to ET-1 and constitutes a regulatory site controlling production of the active peptide.

Neutral endopeptidase (NEP), a zink metallopeptidase, degrades atrial natriuretic peptide (ANP) and constitutes a regulatory site controlling concentration of the active peptide. In serum-deprived pheochromocytoma cells, ANP inhibits apoptosis by causing cGMP elevation. Spreading depression in the cortex is followed by long lasting elevation of the ANP expression and intracellular cGMP concentration. Natriuretic peptide receptor NPrA regulates intracellular cGMP concentration by stimulating particulate guanylyl cyclase (pGC), which activates cGMP-dependent protein kinase G pathway.

Since up-regulation of ET-1 receptors and down-regulation of ANP receptors has been reported to occur in cells subjected to metabolic or oxidative insults, it prompted us to explore the effects of dual ECE/NEP inhibition on rodent cells undergoing apoptosis similar to those reported in humans during ophthalmic diseases such as during e.g. glaucoma.

INDUSTRIAL BACKGROUND OF THE INVENTION

The invention relates to a novel use of benzazepine, benzoxazepine, benzothiazepine-N-acetic acid and phosphono-substituted benzazepinone derivatives having neutral endopeptidase (NEP) and/or human soluble endopeptidase (hSEP) inhibitory activity. The compounds of the invention are useful for the preparation of pharmaceutical compositions for prophylaxis and treatment of ophthalmic diseases.

The invention relates to the use of compounds disclosed in the patent EP1706121 B1 for the manufacture of medicaments giving a beneficial effect. A beneficial effect is disclosed herein or apparent to a person skilled in the art from the specification and general knowledge in the art. The invention also relates to the use of compounds of the invention for the manufacture of medicaments for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medication.

EP1706121 B1 refers to the use of certain compounds with a combined inhibitory activity on both neutral endopeptidase, and/or human soluble endopeptidase (hSEP), and endothelin converting enzyme (ECE) for the treatment and/or prophylaxis of neurodegenerative diseases such as traumatic brain injury, acute disseminated encephalomyelitis, epilepsy related brain damage, spinal cord injury, bacterial or viral meningitis and meningoencephalitis, prion diseases, poisonings with neurotoxic compounds, and radiation-induced brain damage, and for prophylaxis of ischemic stroke, with the proviso that said pharmaceutical compositions do not contain an aldosterone receptor antagonist.

WO 2004/082637, filed on Mar. 18, 2004, and published on Sep. 30, 2004, discloses a method for the prophylaxis or treatment of a very large number of pathological conditions, comprising administering an aldosterone receptor antagonist and an ECE inhibitor. Among the pathological conditions listed are glaucoma, hypertensive or diabetic retinopathy, and elevated intraocular pressure. However, no disclosure regarding the benefit of preferred compounds in these indications was made.

The goal of the present invention was to identify specific metalloprotease inhibitors which are of therapeutic value when administered in a pharmaceutical composition not containing aldosterone receptor antagonist.

Surprisingly, it now has been found that benzazepine, benzoxazepine, benzothiazepine-N-acetic acid and phosphono-substituted benzazepinone derivatives having neutral endopeptidase (NEP) and/or human soluble endopeptidase (hSEP) inhibitory activity prevent apoptosis in rodent models similar to that observed in the course of eye diseases in humans. This property makes them useful for treatment and/or prophylaxis and/or preparation of pharmaceutical compositions for treatment and/or prophylaxis of optic and/or eye diseases selected from the group consisting of such diseases as e.g. (i) all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma; (ii) aquired macular disorders, preferably such as e.g. age-related macular degeneration, idiopathic choroidal neovascularisation, central serous chorioretinopathy, vitreomacular interface disorders, idiopathic macular telangiectasia, cystoid macular oedema, and microcystic macular oedema; (iii) optic neuropathy, preferably such as e.g. anterior or posterior ischemic optic neuropathy; (iv) optic neuritis; (v) uveitis, preferably such as e.g. anterior uveitis, intermediate uveitis, posterior uveitis, and panuveitis; (vi) hereditary fundus dystrophies, preferably such as e.g. retinitis pigmentosa, cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform macular dystrophy, North Carolina macular dystrophy, familial dominant drusen, and concentric annular macular dystrophy; (vii) retinal vascular diseases, preferably such as e.g. diabetic retinopathy, non-diabetic retinopathy, retinal venous occlusive disease, retinal arterial occlusive disease, ocular ischaemic syndrome, hypertensive eye disease, sickle cell retinopathy, thalassemia retinopathy, retinopathy of prematurity, retinal artery macroaneurysm, primary retinal telangiectasia, Eales disease, and radiation retinopathy; (viii) scleritis and episcleritis; (ix) retinal detachments; (x) trauma to the eye globe; (xi) vitreous opacities, preferably such as e.g. vitreous hemorrhage, and asteroid hyalosis; (xii) myopia and degenerative myopia; (xiii) postsurgical trauma, preferably such as e.g. mechanical trauma due to conventional surgery, thermotrauma due to laser surgery, and trauma induced by cryosurgery; (xiv) dry eye disease; (xv) corneal disorders, preferably such as abrasions, lacerations, ulcerations, dystrophies, opacities, endothelial and epithelial decompensation, post-surgical oedema, corneal degenerations, corneal vascularisation; and corneal ectasias, preferably such as keratoconus.

The compounds of the invention are known from the European patents EP 0 733 642, EP 0 916 679 and EP 1 468 010, containing detailed syntheses, and can be described by the general formula (1):

(1)

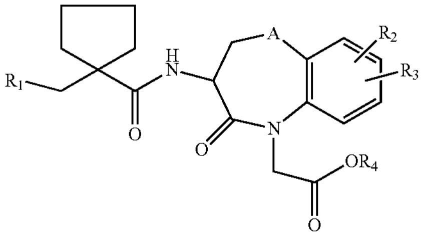

wherein:

R1 stands for a group with formula (2) or (3):

(2)

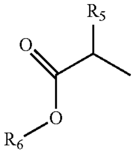

(3)

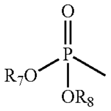

A represents CH2, O or S,

R2 and R3 independently represent hydrogen or halogen,

R4 and R6 independently represent hydrogen or a biolabile carboxylic ester forming group;

R5 is selected from the group consisting of (C1-C6)-alkoxy-(C1-C6)-alkyl which may be substituted by a (C1-C6)-alkoxy, phenyl-(C1-C6)-alkyl and phenyloxy-(C1-C6)-alkyl wherein the phenyl group may be substituted with (C1-C6)-alkyl, (C1-C6)-alkoxy or halogen, and naphtyl-(C1-C6)-alkyl, R7 and R8 independently represent hydrogen or a group forming a biolabile phosphonic acid ester.

To the invention belong all compounds having formula (1), racemates, mixtures of diastereomers and the individual stereoisomers, and also include pharmaceutically acceptable salts thereof. Thus compounds in which the substituents on potentially asymmetrical carbon atoms are in either the R-configuration or the S-configuration belong to the invention.

Pharmaceutically acceptable salts may be obtained using standard procedures well known in the art, for example by mixing a compound of the present invention with a suitable metal cation or an organic base, for instance an amine.

This objective can be achieved by preparing the metal salt of the compounds with the general formula (1) as mentioned above wherein the metal ion is a lithium ion or a bivalent metal ion. Preferred bivalent metal salts are calcium, magnesium and zinc salts. Most preferred is the calcium salt.

The invention relates to the use of a compound of general formula (1), as defined above, for treatment and/or prophylaxis and/or preparation of pharmaceutical compositions for treatment and/or prophylaxis of optic and/or eye diseases selected from the group consisting of such diseases as e.g. (i) all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma; (ii) aquired macular disorders, preferably such as e.g. age-related macular degeneration, idiopathic choroidal neovascularisation, central serous chorioretinopathy, vitreomacular interface disorders, idiopathic macular telangiectasia, cystoid macular oedema, and microcystic macular oedema; (iii) optic neuropathy, preferably such as e.g. anterior or posterior ischemic optic neuropathy; (iv) optic neuritis; (v) uveitis, preferably such as e.g. anterior uveitis, intermediate uveitis, posterior uveitis, and panuveitis; (vi) hereditary fundus dystrophies, preferably such as e.g. retinitis pigmentosa, cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform macular dystrophy, North Carolina macular dystrophy, familial dominant drusen, and concentric annular macular dystrophy; (vii) retinal vascular diseases, preferably such as e.g. diabetic retinopathy, non-diabetic retinopathy, retinal venous occlusive disease, retinal arterial occlusive disease, ocular ischaemic syndrome, hypertensive eye disease, sickle cell retinopathy, thalassemia retinopathy, retinopathy of prematurity, retinal artery macroaneurysm, primary retinal telangiectasia, Eales disease, and radiation retinopathy; (viii) scleritis and episcleritis; (ix) retinal detachments; (x) trauma to the eye globe; (xi) vitreous opacities, preferably such as e.g. vitreous hemorrhage, and asteroid hyalosis; (xii) myopia and degenerative myopia; (xiii) postsurgical trauma, preferably such as e.g. mechanical trauma due to conventional surgery, thermotrauma due to laser surgery, and trauma induced by cryosurgery; (xiv) dry eye disease; (xv) corneal disorders, preferably such as abrasions, lacerations, ulcerations, dystrophies, opacities, endothelial and epithelial decompensation, post-surgical oedema, corneal degenerations, corneal vascularisation; and corneal ectasias, preferably such as keratoconus, with the proviso that said pharmaceutical compositions do not contain an aldosterone receptor antagonist.

Further embodiments of the invention are defined in the dependent claims.

The invention particularly relates to the use of compounds having general formula (4):

(4)

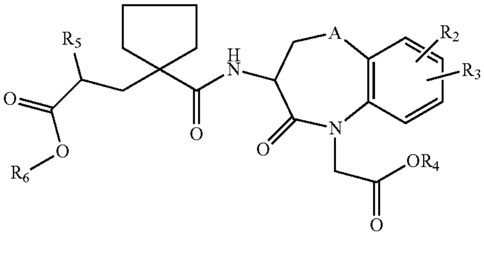

wherein the symbols have the meanings as given above.

More particular, the invention relates to the use of compounds having general formula (5):

(5)

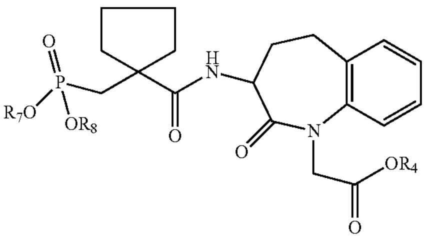

wherein the symbols have the meanings as given above.

The most preferred active substances used according to the present invention are:

(2R)-2-{[1-({[(3S)-1-(carboxymethyl)-2-oxo-2,3,4,5-tetrahydro-1H-1-benzazepin-3-yl]amino}carbonyl)cyclopentyl]methyl}-4-phenylbutanoic acid (6):

(6)

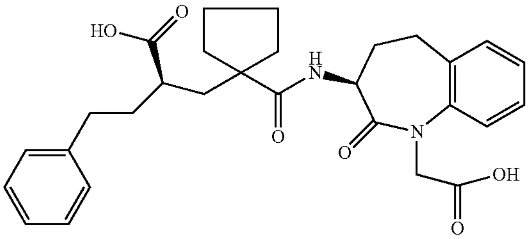

(2R)-2-{[1-({[(3S)-1-(carboxymethyl)-2-oxo-2,3,4,5-tetrahydro-1H-1-benzazepin-3-yl]amino}carbonyl)cyclopentyl]methyl}-4-(1-naphthyl)butanoic acid (7):

(7)

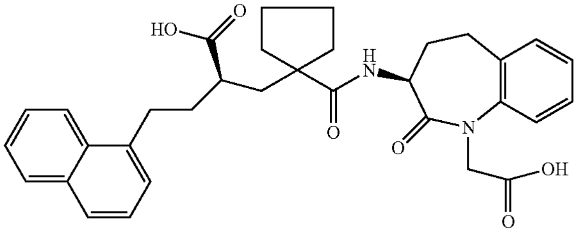

tert-butyl-((3S)-3-{[(1-{[(benzyloxy)(ethoxy)phosphoryl]methyl)cyclopentyl) carbonyl]amino}-2-oxo-2,3,4,5-tetrahydro-1H-1-benzazepin-1-yl)acetate (8):

(8)

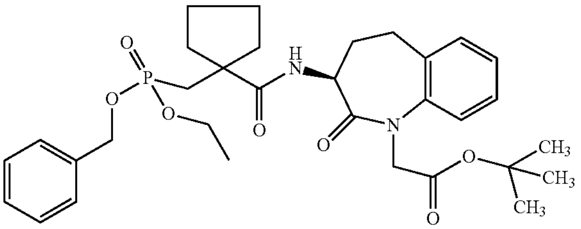

PHARMACEUTICAL COMPOSITIONS

The compounds of the invention can be brought into forms suitable for administration by means of usual processes using auxiliary substances such as liquids or carrier materials. The pharmaceutical compositions of the invention may be administered either topically and/or systemically and in particular e.g. topically to the eye, periocularly in such manner as subconjunctival, subtenon, retrobulbar or peribulbar, intraocularly into the eye, but also enterally, orally, parenterally (intramuscularly or intravenously), subcutaneously or rectally. They can be administered in the form of solutions, suspensions, ointments (creams, gels, gel-forming solutions, sprays, ocular inserts/deposits, contact lenses), ocular implants but also tablets, capsules, softgels, powders, suppositories, nano-formulations or via iontophoresis, or by means of pharmaceutical compositions based on nanoparticle carrier systems. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions. Types of pharmaceutical compositions that may be used include but are not limited to solutions, suspensions, ointments (creams, gels or sprays), but also tablets, chewable tablets, capsules, softgels, parenteral solutions, suppositories, and other types disclosed herein or apparent to a person skilled in the art from the specification and general knowledge in the art. The pharmaceutical compositions of the invention do not contain an aldosterone receptor antagonist.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Very specific formulations suitable for the compounds of the invention have been described in the patent applications WO 03/068266 and WO 04/062692.

The specific compounds described above are intended to further illustrate the invention in more detail, and therefore are not deemed to restrict the scope of the invention in any way.

Eye Diseases: Delayed Retinal Cell Death in Humans and Experimental Models

Apoptosis is a significant component of cell death in optic and/or eye diseases including (i) all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma (R. Agarwal, S. K. Gupta, P. Agarwal, R. Saxena & S. S. Agrawal (2009) Indian J. Ophthalmol. 57, 257-266); (ii) aquired macular disorders, preferably such as e.g. age-related macular degeneration, idiopathic choroidal neovascularisation, central serous chorioretinopathy, vitreomacular interface disorders, idiopathic macular telangiectasia, cystoid macular oedema, and microcystic macular oedema (J. L. Dunaief, T. Dentchev, G.-S. Ying & A. H. Milam (2002) Arch. Ophthalmol. 120, 1435-1442); (iii) optic neuropathy, preferably such as e.g. anterior or posterior ischemic optic neuropathy (B. J. Slater, Z. Mehrabian, Y. Guo, A. Hunter & S. L. Bernstein (2008) Invest. Ophthalmol. Vis. Sci. 49, 3671-3676); (iv) optic neuritis (K. S. Shindler, E. Ventura, M. Dutt & A. Rostami (2008) Exp. Eye Res. 87, 208-213); (v) uveitis, preferably such as e.g. anterior uveitis, intermediate uveitis, posterior uveitis, and panuveitis (C.-C. Chan, D. M. Matteson, Q. Li, S. M. Whitcup & R. B. Nussenblatt (1997) Arch. Ophthalmol. 115, 1559-1567); (vi) hereditary fundus dystrophies, preferably such as e.g. retinitis pigmentosa, cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform macular dystrophy, North Carolina macular dystrophy, familial dominant drusen, and concentric annular macular dystrophy (H. Zhang, X. Li, X. Dai, J. Han, Y. Zhang, Y. Qi, Y. He, Y. Liu, B. Chang & J. J. Pang (2017) J. Ophthalmol. 2017, 1-13 9721362); (vii) retinal vascular diseases, preferably such as e.g. diabetic retinopathy, non-diabetic retinopathy, retinal venous occlusive disease, retinal arterial occlusive disease, ocular ischemic syndrome, hypertensive eye disease, sickle cell retinopathy, thalassemia retinopathy, retinopathy of prematurity, retinal artery macroaneurysm, primary retinal telangiectasia, Eales disease, and radiation retinopathy (G. Donati, A. Kapetanios, M. Dubois-Dauphin & C. J. Pournaras (2008) Acta Ophthalmol. 86, 302-306); (viii) scleritis or episcleritis (C. Heinz, N. Bograd, J. Koch & A. Heiligenhaus (2013) Graefes Arch. Clin. Exp. Ophthalmol. 251, 139-142); (ix) retinal detachments (J. G. Arroyo, L. Yang, D. Bula & D. F. Chen (2005) Am. J. Ophthalmol. 139, 605-610); (x) trauma to the eye globe (H.-C. H. Wang, J.-H. Choi, W. A. Greene, M. L. Plamper, H. E. Cortez, M. Chavko, Y. Li, J. J. Dalle Lucca & A. J. Johnson (2014) Military Med. 179, S34-S40); (xi) vitreous opacities such as e.g. vitreous haemorrhage and asteroid hyalosis (A. Alamri, H. Alkatan & I. Aljadaan (2016) Middle East African J. Ophthalmol. 23, 271-273); (xii) myopia and degenerative myopia (G. Z. Xu, W. W. Li & M. O. Tso (1996) Trans. Am. Ophthalmol. Soc. 94, 411-431); (xiii) postsurgical trauma, preferably such as e.g. mechanical trauma due to conventional surgery, thermotrauma due to laser surgery, and trauma induced by cryosurgery (A. Barak, T. Goldkorn & L. S. Morse (2005) Invest. Ophthalmol. Vis. Sci. 46, 2587-2591; X. Liu, S. Ling, X. Gao, C. Xu & F. Wang (2013) JAMA Ophthalmol. 131, 1070-1072; D. Reichstein (2015) Curr. Opin. Ophthalmol. 26, 157-166); (xiv) dry eye disease (S. Yeh, X. J. Song, D. Q. Li, W. Farley, M. E. Stern & S. C. Pflugfelder (2003) Invest. Ophthalmol. Vis. Sci. 43, 124-129); (xv) corneal disorders, preferably such as abrasions, lacerations, ulcerations, dystrophies, opacities, endothelial and epithelial decompensation, post-surgical oedema, corneal degenerations, corneal vascularisation, and corneal ectasias, preferably such as keratoconus (R. M. Kaldawy, J. Wagner, S. Ching & G. M. Seigel (2002) Cornea 21, 206-209; N. Szentmary, B. Szende & I. Suveges (2005) Eur. J. Ophthalmol. 15, 17-22). In humans, apoptosis has been demonstrated to occur in the course of glaucoma in retinal ganglion cells by means of real-time imaging using annexin 5 labelled with fluorescent dye DY-776 (M. F. Cordeiro, E. M. Normando, M. J. Cardoso, S. Miodragovic, S. Jeylani, B. M. Davis, L. Guo, S. Ourselin, R. A'Hern & P. A. Bloom (2017) Brain 140, 1757-1767). To model this kind of apoptosis in a non-human experiment, rats are subjected to systemic administration of doxorubicin and apoptosis assessed in large organs such as the liver or heart (R. Gillet, G. Grimber, M. Bennoun, C. Caron de Fromentel, P. Briand & V. Joulin (2000) Oncogene 19, 3498-3507; L. L. Fan, G. P. Sun, W. Wei, Z. G. Wang, L. Ge, W. Z. Fu & H. Wang (2010) World J. Gastroenterol. 16, 1473-1481), or rats are subjected to the action of doxorubicin in the eye and apoptosis assessed in the retinal ganglion cells (I. M. Parhad, J. W. Griffin, A. W. Clark & J. F. Koves (1984) J. Neuropathol. Exp. Neurol. 43, 188-200). We used doxorubicin-induced apoptosis in the rat to assess whether systemic administration of compounds example prevents it.

EXAMPLES

Methods: Wistar rats, 200-250 g, were anesthetized with chloral hydrate, 400 mg/kg, and osmotic minipumps, primed prior to implantation, were filled with either vehicle or example (6), representative for the compounds of the invention, in the dose of 60 mg/kg/d, and were implanted subcutaneously. Subsequently, rats (n=7) received doxorubicin in the dose of 5 mg/kg i.p. t.i.d. on days 1, 2 and 3, or rats (n=8) received doxorubicin in the dose of 5 μg or vehicle in the volume of 5 μl into the vitreous body of the eye by means of a Hamilton microsyringe over 5 min on the day 1. Rats were euthanized 5 days after the first i.p. injection of doxorubicin, or 5 days after the administration of doxorubicin into the vitreous body, and were transcardially perfused with a solution containing 4% paraformaldehyde in phosphate buffer. The livers and the eyes were subsequently removed and embedded in paraffin. To visualize apoptosis, a terminal deoxynucleotide transferase-mediated dUTP nick end-label (TUNEL) based staining was performed on 10 μm paraffin sections. The method of stereological disector (L. M. Cruz-Orive & E. R. Weibel (1990) Am. J. Physiol. 258, L148-L156) was used for quantification of apoptosis. An unbiased counting frame (0.05×0.05 mm, disector height 0.01 mm) was used for liver and (0.10×0.025 mm, disector height 0.01 mm) for the retinal ganglion cell layer for the sampling. The $N_v$ of TUNEL positive cells was determined with 8-10 dissectors and is expressed as number of TUNEL positive cells×$10^2$/$mm^3$ for liver and as number of TUNEL positive cells×$10^3$/$mm^3$ for retinal ganglion cells. Statistical evaluation was performed by means of Student's t-test (Table 1).

Results: Doxorubicin caused apoptosis either in the liver or in the retina as evidenced by the presence of TUNEL positive cells (Table 1). Example (6) conferred significant protection against doxorubicin induced apoptosis in the liver and in the retina as evidenced by reduction of $N_v$ of TUNEL positive cells vs vehicle-treated subjects (Table 1).

Conclusions: Example (6) decreased density of apoptotic cells in the rat liver by 23.46% and in the retina by 8.21% (Table 1). The apoptosis induced by doxorubicin in the liver was characterized by many morphological features similar to those of apoptosis seen in the retinal ganglion cells.

TABLE 1

Effect on doxorubicin-induced apoptosis.

| | Doxorubicin + Vehicle $N_v$ | Doxorubicin + Example (6) $N_v$ |
|---|---|---|
| Liver | 10.36 ± 0.55 | 7.93 ± 0.25** |
| % | 100 | 76.54 |
| RGC | 36.65 ± 0.36 | 33.64 ± 0.96* |
| % | 100 | 91.79 |

*P < 0.05,
**P < 0.01 vs doxorubicin + vehicle; Student's t-test; RGC, retinal ganglion cells; $N_v$, number of TUNEL-positiv cells/$mm^3$ ± SEM.

The invention claimed is:

1. A method of decreasing apoptosis in retinal ganglion cells for the treatment of an eye disease, comprising administering to a subject in need thereof a compound of formula (1) wherein:

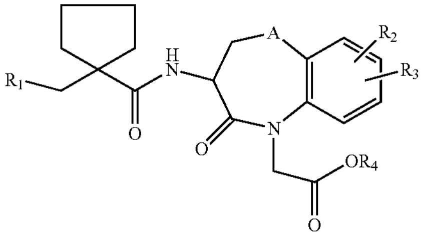

(1)

$R_1$ is a group of formula (2) or (3):

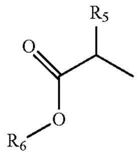

(2)

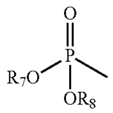

(3)

A is $CH_2$, O or S;

$R_2$ and $R_3$ are independently hydrogen or halogen;

$R_4$ is hydrogen, tert-butyl or a group that forms a biolabile carboxylic ester;

$R_5$ is selected from the group consisting of (C1-C6) alkoxy, (C1-C6)alkyl, (C1-C6)alkyl substituted by a (C1-C6) alkoxy, naphthyl-(C1-C6)-alkyl, phenyl-(C1-C6)-alkyl, and phenyloxy-(C1-C6)-alkyl;

$R_6$ is hydrogen or a group that forms a biolabile carboxylic ester;

$R_7$ and $R_8$ are independently hydrogen, benzyl, ethyl or a group that forms a biolabile phosphonic acid ester;

one or more stereoisomers of the compound of formula (1);

one or more pharmaceutically acceptable salts of the compound of formula (1);

and wherein the eye disease is selected from the group consisting of glaucoma, acquired macular disorders, optic neuropathy, optic neuritis, uveitis, retinal vascular diseases, scleritis, episcleritis, retinal detachments, trauma to eye globe, vitreous opacities, myopia, degenerative myopia, postsurgical trauma, dry eye disease, and corneal disorders.

2. The method of claim 1, wherein in the compound of formula (1) R1 is a group of formula (2), and the compound administered has the formula (4):

(4)

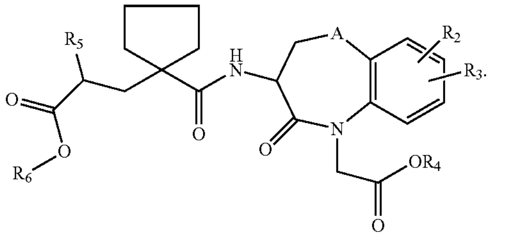

3. The method of claim 1, wherein in the compound of formula (1) $R_1$ is a group of formula (3), and the compound administered has the formula (5):

(5)

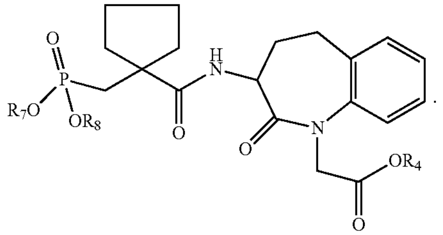

4. The method of claim 1, wherein the compound of formula (1) is (2R)-2-{[1-({[(3S)-1-(carboxymethyl)-2-oxo-2,3,4,5-tetrahydro-1H-1-benzazepin-3-yl]amino carbonyl) cyclopent-yl]methyl}-4-phenylbutanoic acid:

(6)

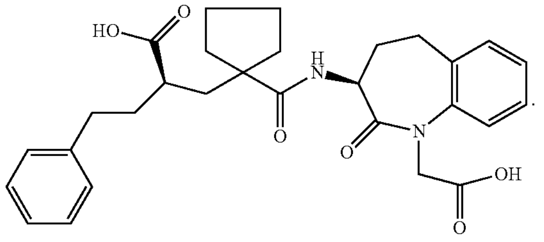

5. The method of claim 1, wherein the compound of formula (1) is (2R)-2-{[(1-({[(3S)-1-(carboxymethyl)-2-oxo-2,3,4,5-tetrahydro-1H-1-benzazepin-3yl]aminoIcarbonyl)cyclopent-yl]methyl}-4-(1-naphthyl) butanoic acid:

(7)

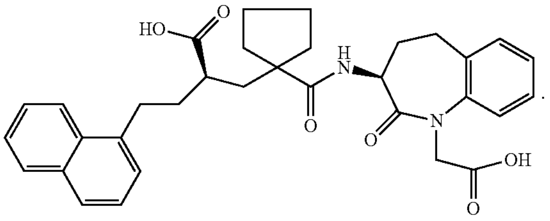

6. The method of claim 1, wherein the compound of formula (1) is tert-butyl-((3S)-3-{[(1-{R benzyloxy) (ethoxy)phosphoryl]methyl}cyclopentyl)-carbonyl]amino)-2-oxo-2,3,4,5-tetrahydro-1H-1-benzazepin-1-yl)acetate:

(8)

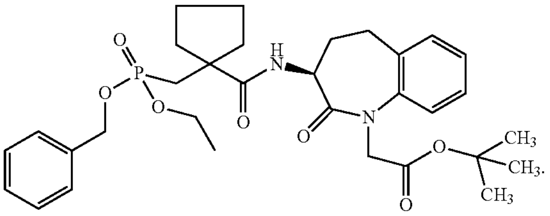

7. The method of claim 1, wherein the pharmaceutically acceptable salt of the compound of formula (1) is selected from the group consisting of a lithium salt, a calcium salt, a magnesium salt, and a zinc salt.

8. The method of claim 7, wherein the pharmaceutically acceptable salt of the compound of formula (1) is the calcium salt.

9. The method of claim 1, wherein the eye disease is glaucoma selected from the group consisting of primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma.

10. The method of claim 1, wherein the eye disease of acquired macular disorders is selected from the group consisting of age-related macular degeneration, idiopathic choroidal neovascularisation, central serous chorioretinopathy, vitreomacular interface disorders, idiopathic macular telangiectasia, cystoid macular oedema, and microcystic macular oedema.

11. The method of claim 1, wherein the eye disease is selected from the group consisting of optic neuropathy; scleritis; episcleritis; optic neuritis; and uveitis.

12. The method of claim 11, wherein the eye disease of optic neuropathy is selected from the group consisting of anterior and posterior ischemic optic neuropathy.

13. The method of claim 11, wherein the eye disease of uveitis is selected from the group consisting of anterior uveitis, intermediate uveitis, posterior uveitis, and panuveitis.

14. The method of claim 1, wherein the eye disease of retinal vascular diseases is selected from the group consisting of diabetic retinopathy, non-diabetic retinopathy, retinal venous occlusive disease, retinal arterial occlusive disease, ocular ischemic syndrome, hypertensive eye disease, sickle cell retinopathy, thalassemia retinopathy, retinopathy of prematurity, retinal artery macroaneurysm, primary retinal telangiectasia, Eales disease, and radiation retinopathy.

15. The method of claim 1, wherein the eye disease is selected from the group consisting of myopia, degenerative myopia, and dry eye disease.

16. The method of claim 1, wherein the eye disease is selected from the group consisting of trauma to the eye globe; postsurgical trauma; vitreous opacities; and retinal detachments.

17. The method of claim 16, wherein the eye disease of postsurgical trauma is selected from the group consisting of mechanical trauma due to conventional surgery, thermotrauma due to laser surgery, and trauma induced by cryosurgery.

18. The method of claim 16, wherein the eye disease of vitreous opacities is selected from the group consisting of vitreous hemorrhage, and asteroid hyalosis.

19. The method of claim 1, wherein the eye disease of corneal disorders is selected from the group consisting of abrasions, lacerations, ulcerations, dystrophies, opacities, endothelial decompensation, epithelial decompensation, post-surgical oedema, corneal degenerations, corneal vascularisation; corneal ectasias, and keratoconus.

20. A method of decreasing apoptosis in retinal ganglion cells for the treatment of an eye disease in a human subject, comprising administering to a subject in need thereof a therapeutically effective amount of a compound having formula (6):

(6)

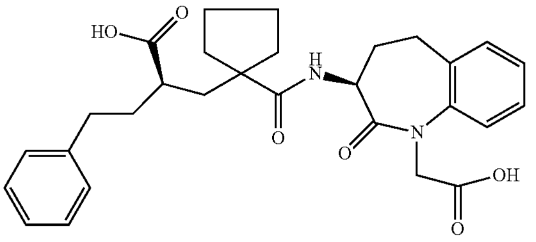

or a pharmaceutically acceptable salt or stereoisomer thereof;

wherein the eye disease is selected from the group consisting of glaucoma, acquired macular disorders, optic neuropathy, optic neuritis, uveitis, retinal vascular diseases, scleritis, episcleritis, retinal detachments, trauma to eye globe, vitreous opacities, myopia, degenerative myopia, postsurgical trauma, dry eye disease, and corneal disorders.

21. The method of claim 20, wherein the compound is administered at a dose of about 60 mg/kg/day.

22. The method of claim 20, wherein the eye disease is glaucoma selected from the group consisting of primary open-angle glaucoma, normal-tension glaucoma, primary angle-closure glaucoma, pseudo-exfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma.

23. A method of decreasing apoptosis in retinal ganglion cells for the treatment of an eye disease in a human subject, comprising administering to a subject in need thereof a therapeutically effective amount of a compound having formula (4), (4)

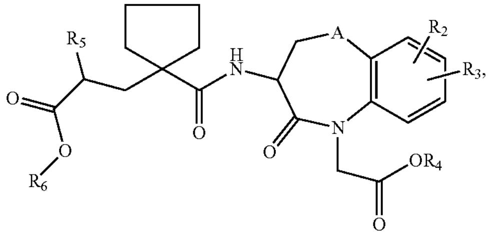

wherein:

A represents $CH_2$, $R_2$ and $R_3$ represent hydrogen, $R_4$ and $R_6$ represent hydrogen or a biolabile carboxylic ester forming group;

$R_5$ is selected from the group consisting of phenyl-(C1-C6)-alkyl and naphthyl-(C1-C6)-alkyl, or a stereoisomer, and a pharmaceutically acceptable salt thereof;

wherein the administration of the compound decreases apoptosis in retinal ganglion cells in the subject thereby treating the eye disease.

24. The method of claim 23, wherein the eye disease is selected from the group consisting of glaucoma, acquired macular disorders, optic neuropathy, optic neuritis, uveitis, retinal vascular diseases, scleritis, episcleritis, retinal detachments, trauma to eye globe, vitreous opacities, myopia, degenerative myopia, postsurgical trauma, dry eye disease, and corneal disorders.

25. The method of claim 23, wherein the eye disease is glaucoma selected from the group consisting of primary open-angle glaucoma, normal-tension glaucoma, primary angle-closure glaucoma, pseudo-exfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma.

26. The method of claim 23, wherein the compound comprises formula (6):

(6)

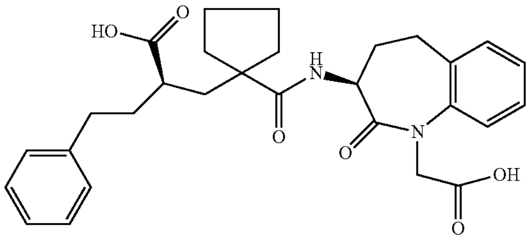

or a pharmaceutically acceptable salt or stereoisomer thereof.

27. The method of claim 23, wherein the compound comprises formula (7):
(7)
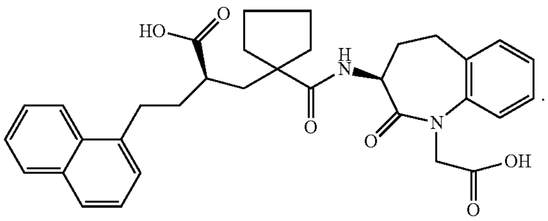
or a pharmaceutically acceptable salt or stereoisomer thereof.
* * * * *